(12) United States Patent
Kim et al.

(10) Patent No.: US 9,333,298 B2
(45) Date of Patent: May 10, 2016

(54) APPARATUS AND METHOD FOR AUTOMATICALLY SUPPLYING INSULIN BASED ON AMOUNT OF EXERCISE

(71) Applicant: Samsung Electronics Co., Ltd., Gyeonggi-do (KR)

(72) Inventors: Jun-Hyung Kim, Gyeonggi-do (KR); Jong-Hyo Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 552 days.

(21) Appl. No.: 13/804,617

(22) Filed: Mar. 14, 2013

(65) Prior Publication Data

US 2013/0274183 A1 Oct. 17, 2013

(30) Foreign Application Priority Data

Apr. 17, 2012 (KR) .......................... 10-2012-0039650

(51) Int. Cl.
*A61M 5/172* (2006.01)
*A61K 38/28* (2006.01)
*A61B 5/00* (2006.01)
*G06F 19/00* (2011.01)
(Continued)

(52) U.S. Cl.
CPC .......... *A61M 5/1723* (2013.01); *A61B 5/14532* (2013.01); *A61B 5/4839* (2013.01); *A61K 38/28* (2013.01); *G06F 19/3468* (2013.01); *G06F 19/3481* (2013.01); *A61B 5/1118* (2013.01); *A61B 5/746* (2013.01); *A61M 2005/14208* (2013.01); *A61M 2205/18* (2013.01); *A61M 2205/3569* (2013.01); *A61M 2205/52* (2013.01)

(58) Field of Classification Search
CPC .................................................. A61M 5/1723
See application file for complete search history.

(56) References Cited

U.S. PATENT DOCUMENTS

| 4,073,292 A | 2/1978 | Edelman |
| 6,269,314 B1 | 7/2001 | Iitawaki et al. |

(Continued)

FOREIGN PATENT DOCUMENTS

| EP | 2 345 893 | 7/2011 | |
| KR | WO 2005110222 A1 * | 11/2005 | ......... A61B 5/14532 |

(Continued)

OTHER PUBLICATIONS

European Search Report dated Dec. 11, 2015 issued in counterpart application No. 13778294.2-1662, 8 pages.

*Primary Examiner* — Laura Bouchelle
(74) *Attorney, Agent, or Firm* — The Farrell Law Firm, P.C.

(57) ABSTRACT

An apparatus and method for automatically supplying insulin based on exercise amount are provided. The apparatus includes a blood sugar measurer for measuring a blood sugar level of a patient; a controller for, comparing the measured blood sugar level with a predetermined blood sugar level, if the measured blood sugar level is greater than or equal to the predetermined blood sugar level, determining whether a current time is within a blood sugar change time zone, if the measured blood sugar level is equal to or higher than the predetermined blood sugar level, and if the current time does is not within the blood sugar change time zone, acquiring exercise amount information about the patient and determining a dose of insulin to be injected inject into the patient based on the acquired exercise amount information, if the current time does not fall within the blood sugar change time zone; and an insulin injector for injecting the determined dose of insulin into the patient.

15 Claims, 4 Drawing Sheets

(51) Int. Cl.
*A61B 5/145* (2006.01)
*A61B 5/11* (2006.01)
*A61M 5/142* (2006.01)

(56) References Cited

U.S. PATENT DOCUMENTS

| | | | | |
|---|---|---|---|---|
| 7,204,823 | B2* | 4/2007 | Estes | A61M 5/14244 604/65 |
| 8,066,640 | B2* | 11/2011 | Angelides | A61K 31/70 435/14 |
| 2007/0060796 | A1 | 3/2007 | Kim | |
| 2009/0209938 | A1* | 8/2009 | Aalto-Setala | A61B 5/02438 604/503 |
| 2012/0046606 | A1 | 2/2012 | Arefieg | |

FOREIGN PATENT DOCUMENTS

| WO | WO 2005/110222 | 11/2005 |
|---|---|---|
| WO | WO 2007/138154 | 12/2007 |
| WO | WO 2009/008612 | 1/2009 |

* cited by examiner

APPARATUS AND METHOD FOR AUTOMATICALLY SUPPLYING INSULIN BASED ON AMOUNT OF EXERCISE

PRIORITY

This application claims priority under 35 U.S.C. §119(a) to a Korean Patent Application filed in the Korean Intellectual Property Office on Apr. 17, 2012 and assigned Serial No. 10-2012-0039650, the entire disclosure of which is incorporated herein by reference.

BACKGROUND OF THE INVENTION

1. Field of the Invention

The present invention relates generally to an apparatus and method for automatically supplying insulin based on the amount of a user's exercise.

2. Description of the Related Art

In general, a diabetic patient does not have a sufficient or normal ability to produce insulin that controls his or her blood sugar. Thus, an insulin injection and/or a special diet help stabilize the blood sugar of a diabetic patient. To continuously supply insulin at a level similar to that of normal pancreatic function, an insulin pump is used.

A decision is made as to whether to inject insulin based on a blood sugar measurement. Normal blood sugar levels range from approximately 70 to 140 milligrams/deciLiter (mg/dL) before and after a meal. Hypoglycemia is defined as a blood sugar level of 70 mg/dL or below. If a diabetic patient's blood sugar is 200 mg/dL or higher, sugar appears in his or her urine. If the blood sugar level reaches 400 mg/dL or higher, an insulin injection is needed. According to a current insulin injection procedure, blood sugar levels are measured before and after a meal and compared with a normal blood sugar range. It is then determined whether to inject insulin based on the comparison. If it is determined that the patient requires insulin, a dose of a required amount of insulin is administered.

An insulin pump injects a preset dose of insulin based on a manual setting. The dose of insulin does not reflect an improvement in a patient's health. That is, the patient's blood sugar level is simply reduced in an artificial manner by injection of an appropriate dose of insulin at each meal.

As described above, the administered dose of insulin should be adjusted for a diabetic patient. Although the same dose of insulin is administered to a diabetic patient every day, the dose of insulin should be adjusted based on meals, physical activity, blood sugar, etc. Thus, an insulin injection may not need to occur regularly. While a change in blood sugar is mostly attributed to eating, an insulin injection is necessary in some cases, for example, when the diabetic patient experiences a rapid change in the amount of exercise or pulse for an unspecified reason.

For instance, when a diabetic patient is exercising, adrenalin production increases from the workout, thus raising a blood sugar level. The blood sugar level rapidly drops after the exercise. Accordingly, if the diabetic patient experiences a change in blood sugar due to unplanned exercise, it is difficult to determine whether the change of blood sugar is caused by a meal or exercise. Therefore, when the blood sugar begins to rise due to exercise, an insulin pump injects insulin, incorrectly assuming that the diabetic patient is eating. As a result, both the post-exercise blood sugar reduction and insulin effects may cause a rapid drop in blood sugar, thereby leading to hypoglycemia.

As a preset dose of insulin is injected unconditionally to a diabetic patient irrespective of a change in blood sugar due to exercise, controlled injection of an appropriate dose of insulin is difficult. Therefore, there exists a need for a method for determining whether to inject insulin adaptively according to whether a patient is exercising.

SUMMARY OF THE INVENTION

An aspect of embodiments of the present invention is to address at least the problems and/or disadvantages and to provide at least the advantages described below. Accordingly, an aspect of embodiments of the present invention is to provide an automatic insulin supply apparatus and method for adaptively adjusting the dose of insulin for a diabetic patient based on a change in the amount of exercise taken by the diabetic patient.

In accordance with an embodiment of the present invention, an apparatus for automatically supplying insulin based on exercise amount. The apparatus includes a blood sugar measurer for measuring a blood sugar level of a patient; a controller for, comparing the measured blood sugar level with a predetermined blood sugar level, if the measured blood sugar level is greater than or equal to the predetermined blood sugar level, determining whether a current time is within a blood sugar change time zone, and if the current time is not within the blood sugar change time zone, acquiring exercise amount information about the patient and determining a dose of insulin to inject into the patient based on the acquired exercise amount information; and an insulin injector for injecting the determined dose of insulin into the patient.

In accordance with another embodiment of the present invention, a method for automatically supplying insulin based on exercise amount in an automatic insulin supply apparatus is provided. The method includes receiving a blood sugar level of a patient measured by a blood sugar sensor; comparing the measured blood sugar level with a predetermined blood sugar level; if the measured blood sugar level is greater than or equal to the predetermined blood sugar level, determining whether a current time is within a blood sugar change time zone; if the current time is not within the blood sugar change time zone, acquiring exercise amount information about the patient; determining a dose of insulin to inject into the patient based on the acquired exercise amount information; and injecting the determined dose of insulin through an insulin injector into the patient.

BRIEF DESCRIPTION OF THE DRAWINGS

The above and other aspects, objects, features and advantages of certain embodiments of the present invention will be more apparent from the following detailed description taken in conjunction with the accompanying drawings, in which.

DETAILED DESCRIPTION OF EMBODIMENTS OF THE PRESENT INVENTION

Reference will be made to embodiments of the present invention with reference to the attached drawings. While specific details such as an outlet, a transistor, a microcomputer, etc. are described in the following description, they are provided to help comprehensive understanding of the present invention. It will be clearly understood to those skilled in the art that variations or modifications can be made to the specific details within the scope and spirit of the present invention. A detailed description of a generally known function and structure of the present invention may be omitted so as not to obscure the subject matter of the present invention.

The present invention provides a method for adaptively adjusting the dose of insulin based on a change in the amount of exercise of a diabetic patient and supplying the adjusted dose of insulin. To accomplish this, the blood sugar level of the diabetic patient is measured and compared with a predetermined blood sugar level. If the measured blood sugar level is greater than or equal to the predetermined blood sugar level, it is determined whether a current time is within a blood sugar change time zone. The blood sugar change time zone means a time zone that blood sugar changes according to a regular meal. If the current time is not within the blood sugar change time zone, a dose of insulin is calculated based on a measurement of exercise amount and the calculated dose of insulin is injected. Therefore, exercise that the diabetic patient takes shortly after a meal, and thus with high blood sugar, is automatically sensed and a dose of insulin can be adjusted, taking into account the unplanned exercise. Consequently, the probability of hypoglycemia is decreased for the diabetic patient.

Figure 1:
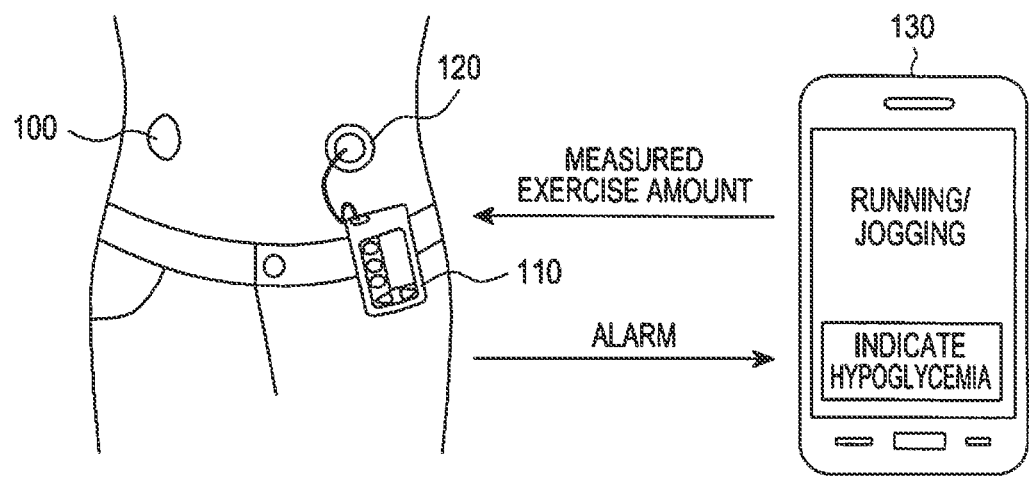
FIG. 1 illustrates the exterior of an automatic insulin supply apparatus according to an embodiment of the present invention.

With reference to FIG. 1, an operation of an automatic insulin supply apparatus having the above-described function will be described below.

Referring to FIG. 1, a blood sugar measurer 100 measures a blood sugar level in response to a control signal received from an automatic insulin supply apparatus 110 or a patient's selective input signal and then outputs the measured blood sugar level to the automatic insulin supply apparatus 110.

The automatic insulin supply apparatus 110 determines whether to inject insulin and the dose of insulin to be injected based on the measured blood sugar level and injects the determined dose of insulin through an insulin injector 120. The insulin injector 120 may be a syringe for injecting insulin into the patient. According to an embodiment of the present invention, the automatic insulin supply apparatus 110 determines in real time whether and how much a diabetic patient has exercised and then determines how much blood sugar has been consumed for the exercise in order to overcome the difficulty involved in adjusting a dose of insulin to be injected in view of an the unplanned exercise. To avoid the situation in which a decreased blood sugar level resulting from the exercise leads to hypoglycemia, the automatic insulin supply apparatus 110 takes into account the amount of exercise in the dose of insulin. Additionally, if a diabetic patient with high blood sugar exercises, for example, shortly after eating, the automatic insulin supply apparatus 110 warns the diabetic patient that hypoglycemia can occur.

While an exercise amount sensor for measuring the amount of exercise done by a patient is included inside the automatic insulin supply apparatus 110, it may be instead incorporated into a mobile terminal 130 as illustrated in FIG. 1. The automatic insulin supply apparatus 110 controls a dose of insulin to be injected into the patient based on the exercise amount measurement received from the exercise amount sensor. If hypoglycemia is expected from an exercise amount measurement after a mealtime or a blood sugar level measurement resulting from unplanned exercise is at a threshold for hypoglycemia, the automatic insulin supply apparatus 110 alerts the patient to stop the exercise by transmitting an alarm to the mobile terminal 130.

Figure 2:
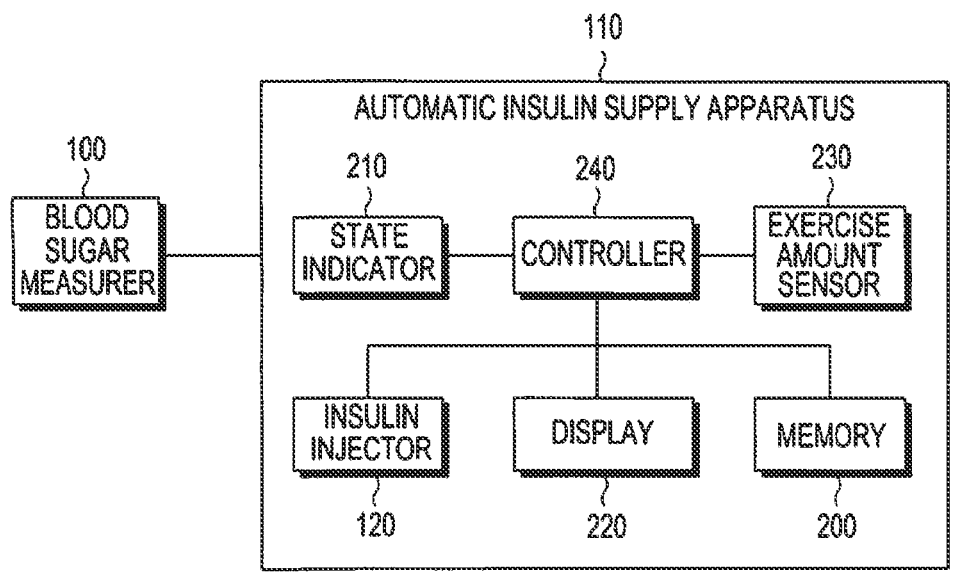
FIG. 2 illustrates a block diagram of an automatic insulin supply apparatus according to an embodiment of the present invention.
Figure 3:
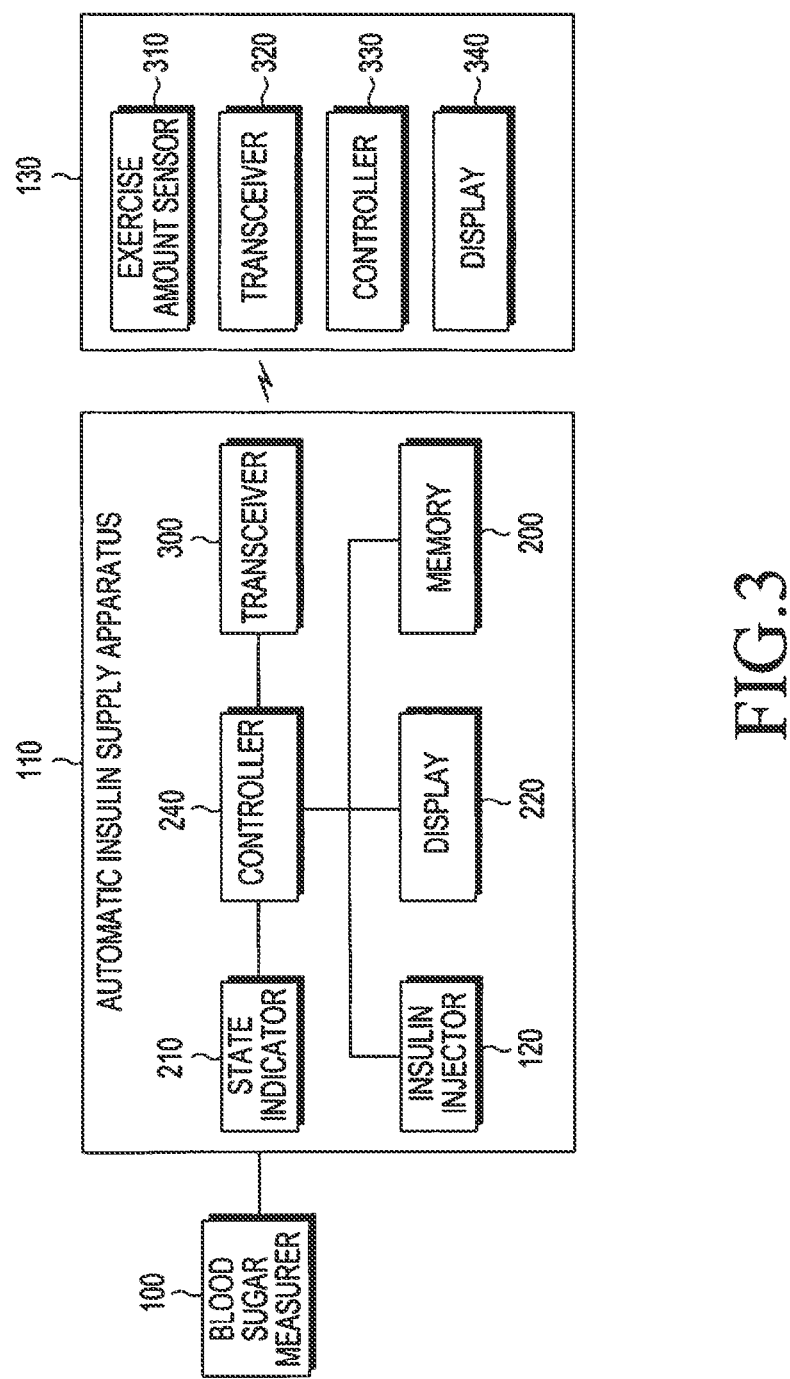
FIG. 3 illustrates a block diagram of an automatic insulin supply apparatus according to another embodiment of the present invention.

The automatic insulin supply apparatus 110 has an internal configuration illustrated in FIG. 2 and FIG. 3. The automatic insulin supply apparatus 110 is provided with an exercise amount sensor in the illustrated case of FIG. 2, whereas the mobile terminal 130 is substituted for the exercise amount sensor in the illustrated case of FIG. 3.

Referring to FIG. 2, the automatic insulin supply apparatus 110 includes a memory 200, a state indicator 210, a display 220, an exercise amount sensor 230, a controller 240, and the insulin injector 120. The automatic insulin supply apparatus 110 further includes the blood sugar measurer 100. While the blood sugar measurer 100 is illustrated in FIG. 1 as detachable from the automatic insulin supply apparatus 110 as an example, the blood sugar measurer 100 can also be integrated into the automatic insulin supply apparatus 110. The blood sugar measurer 100 is, for example, a blood sugar sensor.

The controller 240 receives a blood sugar level measurement from the blood sugar measurer 100 and determines whether and how much insulin to inject based on the received blood sugar level measurement. Thus, the insulin injector 120 injects the determined dose of insulin into a patient under the control of the controller 240.

In accordance with an embodiment of the present invention, the controller 240 acquires exercise amount information measured by the exercise amount sensor 230 and adjusts a dose of insulin according to the exercise amount or controls the output of an alarm sound or message to alert the patient to stop exercising.

The memory 200 stores data related to the patient. The memory 200 automatically stores data such as blood sugar levels in time order (i.e. a blood sugar change record), a dose of insulin, an exercise amount, living pattern information, etc., without the need for inputting data each time. Living pattern information means a pattern that blood sugar changes in accordance with meals, exercise, etc. For instance, if the living pattern information is used, an increase in a blood sugar level according to planned exercise and a regular meal can be inferred when the blood sugar level increases. Accordingly, the controller 240 controls insulin injection in a more organized manner using the data stored in the memory 200. Specifically, upon the receipt of a measured blood sugar level, the controller 240 checks whether the blood sugar level has been increased above a predetermined range. If the blood sugar level is above the predetermined range, the controller 240 analyzes a blood sugar change history using the data stored in the memory 200, for example, the blood sugar change record and the living pattern information.

The state indicator 210 indicates an insulin injection result. If the measured blood sugar level falls within a hypoglycemia range, the state indicator 210 also feeds back information about the state of the patient or outputs an alarm. This state indicator 210 is an alarm generator for sounding an alarm.

The display 220 displays a dose of injected insulin, a remaining dose of insulin, an insulin injection result, and state information about the automatic insulin supply apparatus 100.

The exercise amount sensor 230 is a sensor that senses movement of the patient. That is, the exercise amount sensor 230 senses movement of the automatic insulin supply apparatus 110 accompanying physical activity of the patient. The exercise amount sensor 230 is, for example, a step counter, an acceleration sensor, and the like. Upon sensing movement of the patient, the exercise amount sensor 230 outputs an exercise amount measurement based on the patient's movement.

Accordingly, the controller 240 determines a dose of insulin to be injected based on the blood sugar level measurement and the exercise amount measurement.

FIG. 3 illustrates the structure of the automatic insulin supply apparatus 110 and the mobile terminal 130, when the mobile terminal 130 measures the amount of exercise.

The automatic insulin supply apparatus 110 has the same components and performs the same operation as illustrated in FIG. 2 except that an exercise amount sensor 310 is included in the mobile terminal 130 and the automatic insulin supply apparatus 110 includes a transceiver 300 for communicating with the mobile terminal 130.

The mobile terminal 130 includes an exercise amount sensor 310, a transceiver 320 for communicating with the automatic insulin supply apparatus 110, a controller 330, and a display 340.

The transceiver 300 of the automatic insulin supply apparatus 110 transmits a notification message indicating the blood sugar level of the patient has dropped to a level corresponding to hypoglycemia. Moreover, the transceiver 300 controls a dose of insulin according to a measured exercise amount and feeds back the control result.

The transceiver 320 of the mobile terminal 130 exchanges data with the automatic insulin supply apparatus 110. According to an embodiment of the present invention, the transceiver 320 wirelessly communicates using Bluetooth, for example. The transceiver 320 notifies the transceiver 300 of the automatic insulin supply apparatus 110 of a measured exercise amount and receives a notification message or feedback of a control result from the transceiver 300.

Upon a user's execution of an insulin control application, the controller 330 activates the exercise amount sensor 310. Upon receipt of a notification message or a feedback of a control result, the controller 330 displays the notification message or feedback on the display 340 to notify the patient that exercise increases the risk of hypoglycemia.

In this manner, the automatic insulin supply apparatus 110 increases or decreases a predetermined injection dose of insulin within a range defined by upper and lower limits according to blood sugar information and/or an exercise amount in order to prevent hypoglycemia according to an embodiment of the present invention. A decision of whether to inject insulin is based on a measurement of blood sugar. Normal blood sugar levels are defined as being in a range of 70 to 140 mg/dL before and after meals. A blood sugar level equal to or lower than 70 mg/dL is defined as hypoglycemia. At a blood sugar level greater than or equal to 200 mg/dL, sugar appears in urine. Insulin injection is needed at or above 400 mg/dL.

An operation for injecting insulin according to an embodiment of the present invention will be described below with reference to FIG. 4.

Figure 4:
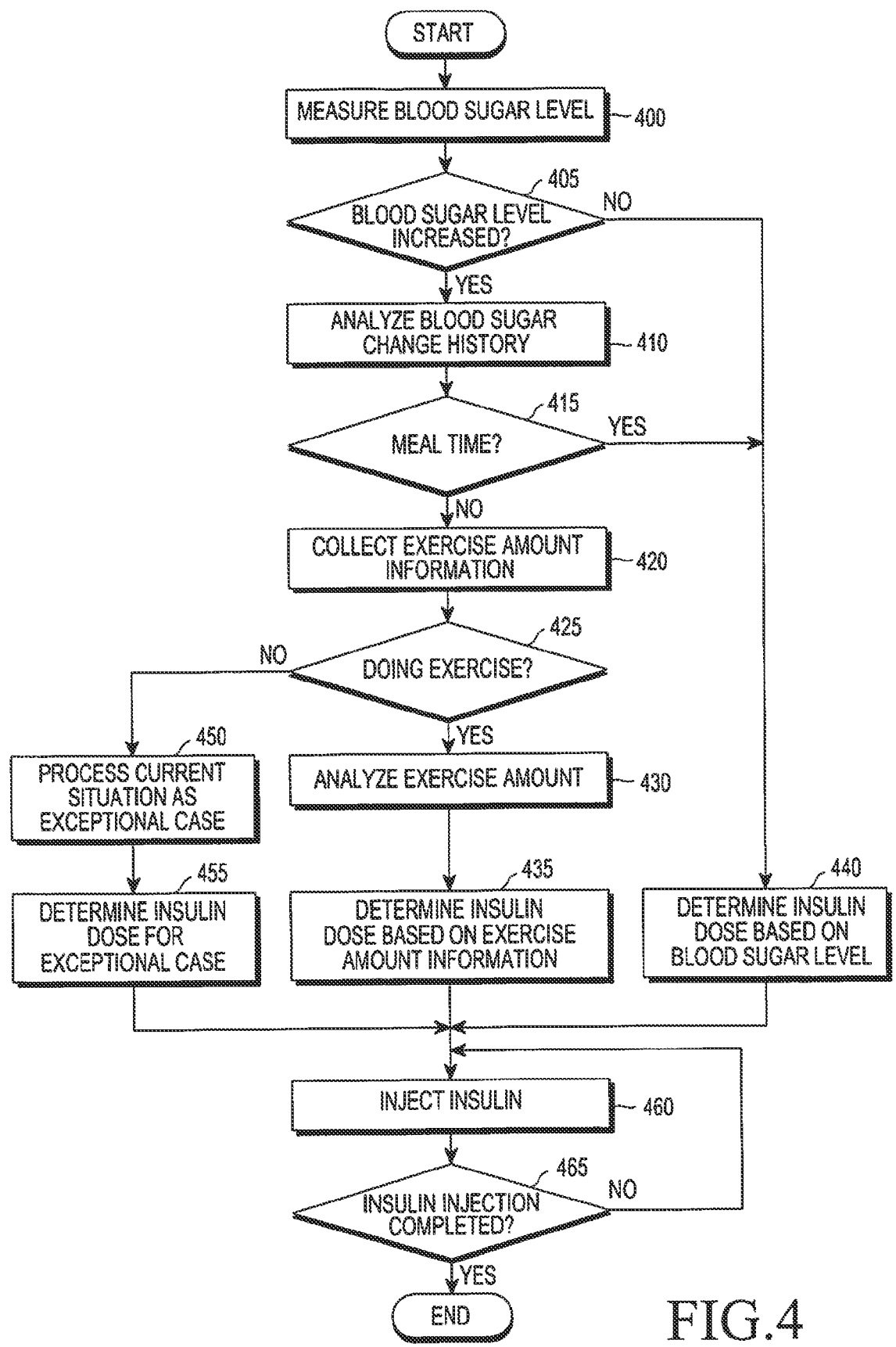
FIG. 4 is a flowchart illustrating an insulin injection operation according to an embodiment of the present invention.

Referring to FIG. 4, the automatic insulin supply apparatus 110 measures a blood sugar level in step 400. The blood sugar level of a patient is measured at predetermined intervals or at other necessary times. Blood sugar levels are collected for a predetermined time period. If the measured blood sugar level is above a predetermined range, that is, the blood sugar level has increased significantly, the automatic insulin supply apparatus 110 analyzes a blood sugar change history in step 410. In this analysis, the automatic insulin supply apparatus 110 uses a pre-stored blood sugar change record and patient living pattern information. If the measured blood sugar level is within the predetermined range, the automatic insulin supply apparatus 110 determines a dose of insulin, taking into account the current blood sugar level in step 440.

The automatic insulin supply apparatus 110 determines whether a current time corresponds to a blood sugar change time zone as a result of the analysis of the blood sugar change history. For example, the automatic insulin supply apparatus 110 determines whether the patient is eating using the per-time zone blood sugar change record in step 415.

If the current time corresponds to mealtime, the automatic insulin supply apparatus 110 determines that the blood sugar level has increased due to the meal. Thus, the automatic insulin supply apparatus 110 determines a dose of insulin, taking into account the current blood sugar level in step 440. In this manner, when the automatic insulin supply apparatus 110 determines that it is mealtime, it increases the dose of insulin, taking into account an increase in blood sugar caused by the meal. In general, there are two types of insulin doses: a basic insulin dose which is a predetermined small amount set to be injected at predetermined intervals and a higher insulin dose to reduce a blood sugar level increased by a meal.

If the current time does not correspond to mealtime, the automatic insulin supply apparatus 110 collects exercise amount information regarding the current exercise state of the patient from the exercise amount sensor in step 420. If the automatic insulin supply apparatus 110 determines that the patient is doing exercise based on the collected exercise amount information in step 425, it analyzes the exercise amount in step 430. The automatic insulin supply apparatus 110 then determines a dose of insulin, taking into account the exercise amount information in step 435. The dose of insulin based on the exercise amount information is less than the dose of insulin in relation to a meal, in the case that a blood sugar level drops after exercise. The upper and lower limits of the basic insulin dose, the meal-based insulin dose, and the exercise-based insulin dose are preset, taking into account patients' medical well being. Preferably, the exercise-based insulin dose is set empirically and statistically from a medical wellbeing standpoint.

If the amount of exercised is determined to be greater than or equal to a predetermined amount based on the collected exercise amount information, the automatic insulin supply apparatus 110 checks a blood sugar change caused by the exercise amount. If the blood sugar change exceeds a threshold range, the automatic insulin supply apparatus 110 warns the patient to stop exercising.

If the automatic insulin supply apparatus 110 determines that the patient is not exercising in step 425, it determines the situation to be exceptional in step 450 and determines a dose of insulin for such an exceptional situation in step 455. An example of an exceptional situation is that when medicine is taken through a separate medicine sensor, the dose of insulin is adjusted according to the taken medicine.

Once the dose of insulin is determined in the above procedure, the automatic insulin supply apparatus 110 injects insulin in step 460 and determines whether the insulin has been completely injected in step 465. Upon completion of the insulin injection, the automatic insulin supply apparatus 110 ends the insulin control operation.

As described above, when a patient experiences a blood sugar change due to exercise at an unscheduled time, the automatic insulin supply apparatus 110 can identify whether the blood sugar change is attributed to a meal or exercise. When the blood sugar level has been increased by exercise, the automatic insulin supply apparatus 110 injects a dose of insulin set based on exercise amount information, thereby preventing hypoglycemia. Therefore, rapid hypoglycemia is prevented, which may otherwise occur due to the addition of a post-exercise blood sugar drop and insulin effects when the cause of a blood sugar increase is incorrectly identified as a meal instead of exercise.

Figure 5:
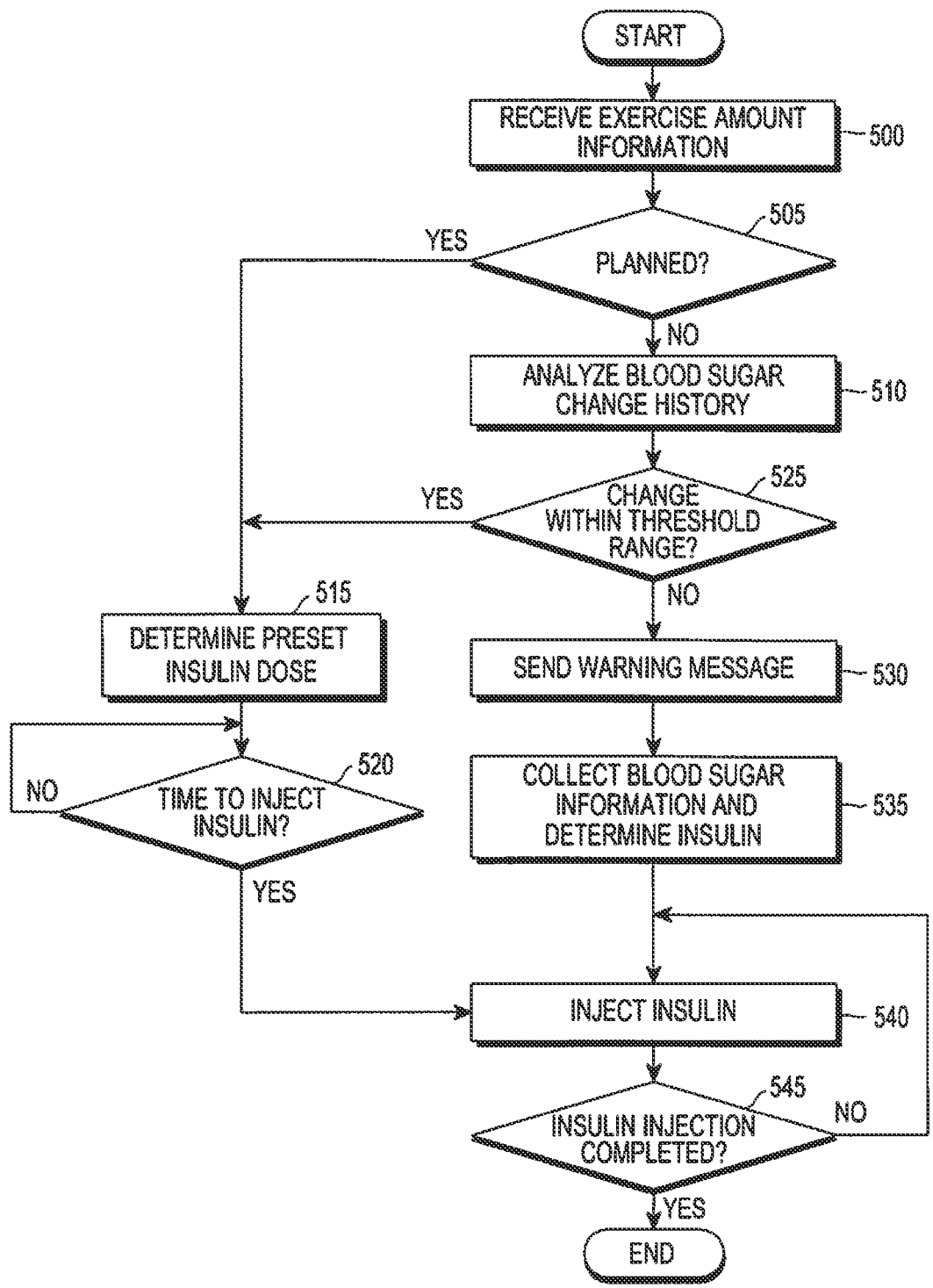
FIG. 5 is a flowchart illustrating an insulin injection operation according to another embodiment of the present invention.

With reference to FIG. 5, an insulin injection operation according to another embodiment of the present invention will be described below. Compared to the foregoing embodiment of the present invention in which a dose of insulin to be injected is adjusted according to a blood sugar change and the amount of exercise, another embodiment of the present invention provides a method for outputting a warning message requesting to control the amount of exercise and accordingly determining an injection dose of insulin, when it is determined based on exercise information that a blood sugar change is greater than or equal to a threshold. Steps 420 to 435 of FIG. 4 are equivalent to steps 500 to 535 of FIG. 5. Thus, exercise amount information is collected, it is determined that a patient is taking exercise based on the collected exercise amount information, and it is determined whether the exercise was planned in step 420 of FIG. 4. If a blood sugar change is above a threshold range, a warning message is transmitted and blood sugar information is again collected. An injection dose of insulin is then determined according to the collected blood sugar information.

In accordance with this embodiment, if a user exercises with high blood sugar (such as shortly after a meal) is sensed and stopping exercise is recommended, thereby preventing hypoglycemia.

The automatic insulin supply apparatus 110 measures the amount of exercise of a patient through the exercise amount sensor and determines whether the patient is taking exercise in step 500. Upon receipt of exercise amount information indicating that the patient is exercising, the automatic insulin supply apparatus 110 determines based on the living pattern information about the patient whether the exercise was planned in step 505. Specifically, it is determined whether the patient is exercising as much as planned at a regular time.

If the exercise is occurring as regularly planned, the automatic insulin supply apparatus 110 determines a preset basic insulin dose in step 515. The preset basic insulin dose is the dose of insulin set based on exercise amount information. If it is time to inject insulin in step 520, the automatic insulin supply apparatus 110 injects the determined dose of insulin in step 540.

However, if the exercise is occurring unexpectedly, for example, if the exercise is occurring at an irregular time according to the living pattern or if the exercise amount exceeds a predetermined amount, the automatic insulin supply apparatus 110 measures a blood sugar change caused by the exercise and analyzes a blood sugar change history by comparing the measured blood sugar change with a pre-stored blood sugar change record in step 510. More specifically, when the patient is exercising, sugar is dissolved and used as a source of energy. Therefore, even though the patient has high blood sugar, the blood sugar level drops due to exercise. Accordingly, the basic dose of insulin that is usually injected should be reduced.

Thus, the automatic insulin supply apparatus 110 determines whether the blood sugar change caused by exercise falls within a threshold range in step 525. If the exercise-caused blood sugar change is greater than the threshold range, the automatic insulin supply apparatus 110 outputs a warning message to the patient or the mobile terminal 130, requesting the patient to stop exercising due to a risk of hypoglycemia increased by overexercise in step 530. However, if the exercise-caused blood sugar change is within the threshold range, the automatic insulin supply apparatus 110 determines the preset basic insulin dose in step 515. Subsequently, the automatic insulin supply apparatus 110 collects blood sugar information to monitor a blood sugar change again and determines a dose of insulin based on the collected blood sugar information in step 535. Once the dose of insulin is determined, insulin is injected in step 540. Upon completion of the insulin injection in step 545, the automatic insulin supply apparatus 110 ends the above procedure.

As described above, mealtimes and exercise states are monitored in advance before a hypoglycemic situation occurs. A dose of insulin to be injected is then determined according to the amount of exercise, thereby preventing hypoglycemia caused by overexercise or unplanned exercise.

As is apparent from the above description of the present invention, the automatic insulin supply apparatus adjusts a dose of insulin to be injected adaptively according to an exercise-caused change in blood sugar. Therefore, hypoglycemia caused by overexercise or unplanned exercise can be prevented. The automatic insulin supply apparatus can also automatically determine that a diabetic patient is exercising with high blood sugar in such a situation as shortly after a meal and can recommend or alert the patient to stop the exercise, thereby reducing the probability of hypoglycemia.

The embodiments of the present invention can be implemented in hardware, software, or a combination of hardware and software. The software can be recorded to a volatile or non-volatile storage device such as a Read-Only Memory (ROM) irrespective of deletable or re-recordable, to a memory such as a Random Access Memory (RAM), a memory chip, a memory device, or an integrated circuit, or to a storage medium that is optically or magnetically recordable and readable by a machine (e.g. a computer), such as a Compact Disc (CD), a Digital Versatile Disc (DVD), a magnetic disk, or a magnetic tape. The storage is an example of a machine-readable storage medium suitable for storing a program or programs including instructions to implement the embodiments of the present invention. Accordingly, the present invention includes a program including a code for implementing the method as appended in the claims and a machine-readable storage medium that stores the program. The program may be transferred electronically through any medium such as a communication signal transmitted through a wired or wireless connection and the present invention embraces equivalents thereof.

In addition, the automatic insulin supply apparatus or the mobile terminal can receive and store the program from a wirelessly or wired connected program providing device. The program providing device may include a program with instructions that make the automatic insulin supply apparatus or the mobile terminal perform the method for automatically supplying insulin according to an exercise amount, a memory for storing information needed for the method, a communication unit for conducting a wired or wireless communication with the automatic insulin supply apparatus or the mobile terminal, and a controller for transmitting the program to the automatic insulin supply apparatus or the mobile terminal upon request of the automatic insulin supply apparatus or the mobile terminal, or automatically.

While the present invention has been particularly shown and described with reference to certain embodiments thereof, it will be understood by those of ordinary skill in the art that various changes in form and details may be made therein without departing from the spirit and scope of the present invention as defined by the following claims and their equivalents.

What is claimed is:

1. An apparatus for automatically supplying insulin based on exercise amount, the apparatus comprising:
   a blood sugar measurer for measuring a blood sugar level of a patient;
   a controller for:
      comparing the measured blood sugar level with a predetermined blood sugar level,
      if the measured blood sugar level is greater than or equal to the predetermined blood sugar level, determining whether a current time is within a blood sugar change time zone,
      if the current time is within the blood sugar change time zone, determining a dose of insulin to inject into the patient based on the measured blood sugar level, and
      if the current time is not within the blood sugar change time zone, acquiring exercise amount information about the patient and determining the dose of insulin to inject into the patient based on the acquired exercise amount information; and
   an insulin injector for injecting the determined dose of insulin into the patient.

2. The apparatus of claim 1, further comprising an exercise amount measurer for acquiring the exercise amount information about the patient.

3. The apparatus of claim 1, wherein the controller further receives the exercise amount information from a mobile terminal through short-range wireless communication.

4. The apparatus of claim 1, further comprising a memory for storing a blood sugar change record of the patient and living pattern information about the patient.

5. The apparatus of claim 4, wherein, if the measured blood sugar level is greater than or equal to the predetermined blood sugar level, the controller further determines whether the current time falls within the blood sugar change time zone by reading the blood sugar change record.

6. The apparatus of claim 1, wherein the controller further determines whether the patient is exercising based on the acquired exercise amount information and, if the patient is exercising, determines the dose of insulin based on the acquired exercise amount information.

7. The apparatus of claim 4, wherein the controller further determines whether the exercise was planned based on the living pattern information about the patient, determines a blood sugar change based on the exercise amount information if the exercise was not planned, and if the blood sugar change is above a threshold range, warns the patient to stop exercising.

8. The apparatus of claim 7, wherein the controller further measures another blood sugar level of the patient through the blood sugar measurer and determines a dose of insulin based on the measured blood sugar level, after warning the patient to stop the exercise.

9. A method for automatically supplying insulin based on exercise amount in an automatic insulin supply apparatus, the method comprising:
   receiving a blood sugar level of a patient measured by a blood sugar sensor;
   comparing the measured blood sugar level with a predetermined blood sugar level;
   if the measured blood sugar level is greater than or equal to the predetermined blood sugar level, determining whether a current time is within a blood sugar change time zone;
   if the current time is within the blood sugar change time zone, determining a dose of insulin to inject into the patient based on the measured blood sugar level;
   if the current time is not within the blood sugar change time zone, acquiring exercise amount information about the patient and determining the dose of insulin to inject into the patient based on the acquired exercise amount information; and
   injecting the determined dose of insulin through an insulin injector into the patient.

10. The method of claim 9, wherein the exercise amount information about the patient is acquired from an exercise amount sensor in the automatic insulin supply apparatus.

11. The method of claim 9, wherein acquiring the exercise amount information about the patient comprises receiving the exercise amount information from a mobile terminal through short-range wireless communication.

12. The method of claim 9, wherein determining whether a current time is within a blood sugar change time zone comprises determining whether the current time falls within the blood sugar change time zone by reading a pre-stored blood sugar change record.

13. The method of claim 9, wherein determining the dose of insulin comprises:
   determining whether the patient is exercising based on the acquired exercise amount information; and
   determining the dose of insulin based on the acquired exercise amount information, if the patient is exercising.

14. The method of claim 9, further comprising:
   determining whether the exercise was planned based on living pattern information about the patient, when acquiring the exercise amount information;
   if exercise was not planned, determining a blood sugar change based on the exercise amount information; and
   if the blood sugar change is above a threshold range, warning the patient to stop the exercise.

15. The method of claim 14, further comprising:
   measuring another blood sugar level of the patient; and
   after warning the patient to stop the exercise, determining a dose of insulin based on the measured blood sugar level.

* * * * *